United States Patent [19]
Albert et al.

[11] Patent Number: 5,735,285
[45] Date of Patent: Apr. 7, 1998

[54] METHOD AND HAND-HELD APPARATUS FOR DEMODULATING AND VIEWING FREQUENCY MODULATED BIOMEDICAL SIGNALS

[75] Inventors: David E. Albert; Landgrave T. Smith, both of Oklahoma City; Carl J. Rieger, Ponca City; Colin J. Cumming, Stillwater, all of Okla.; Leslie D. Hoy, Knoxville, Tenn.

[73] Assignee: Data Critical Corp., Oklahoma City, Okla.

[21] Appl. No.: 658,236

[22] Filed: Jun. 4, 1996

[51] Int. Cl.$^6$ ............................................. A61B 5/0432
[52] U.S. Cl. .......................... 128/696; 128/904; 128/710
[58] Field of Search .......................... 128/696, 710, 128/711, 904; 364/413.03–413.06; 607/32, 60

[56] References Cited

U.S. PATENT DOCUMENTS

| | | | |
|---|---|---|---|
| 3,731,311 | 5/1973 | Williams | 343/17.2 PC |
| 3,882,277 | 5/1975 | DePedro et al. | |
| 3,909,599 | 9/1975 | Trott, Jr. et al. | |
| 4,027,146 | 5/1977 | Gilmore | |
| 4,409,984 | 10/1983 | Dick | 128/696 |
| 4,531,527 | 7/1985 | Reinhold, Jr. et al. | 128/696 |
| 4,567,883 | 2/1986 | Langer et al. | 128/696 |
| 4,803,625 | 2/1989 | Fu et al. | 364/413.03 |
| 4,938,229 | 7/1990 | Bergelson et al. | 128/696 |
| 5,023,906 | 6/1991 | Novas | 379/372 |
| 5,191,891 | 3/1993 | Righter | 128/710 |
| 5,321,618 | 6/1994 | Gessman | 364/413.06 |
| 5,333,616 | 8/1994 | Mills et al. | 128/696 |
| 5,336,245 | 8/1994 | Adams et al. | 607/32 |
| 5,339,824 | 8/1994 | Engira | 128/712 |
| 5,365,935 | 11/1994 | Righter et al. | 128/710 |
| 5,433,736 | 7/1995 | Nilsson | 607/32 X |
| 5,466,246 | 11/1995 | Silvian | 607/32 |
| 5,503,158 | 4/1996 | Coppock et al. | 128/696 |
| 5,544,661 | 8/1996 | Davis et al. | 128/700 |

FOREIGN PATENT DOCUMENTS

2181554  4/1987  United Kingdom ............. 128/710

*Primary Examiner*—Jeffrey R. Jastrzab
*Attorney, Agent, or Firm*—Dougherty & Hessin, P.C.

[57] ABSTRACT

Method and apparatus for transmission of biomedical waveform data from a patient to an attending physician wherein the waveform data audio signal is frequency modulated for subsequent wireline or wireless transmission to a remote hand-held computer that functions to digitize, record and demodulate the frequency modulated signal for display on the computer, for permanent print-out, or for further retransmission.

14 Claims, 5 Drawing Sheets

METHOD AND HAND-HELD APPARATUS FOR DEMODULATING AND VIEWING FREQUENCY MODULATED BIOMEDICAL SIGNALS

A Microfiche Appendix is included in the application

BACKGROUND OF THE INVENTION

1. Field of the Invention.

The invention relates generally to improved method and apparatus for monitoring a patient's biomedical waveform data and, more particularly, but not by way of limitation, it relates to an improved method and apparatus for monitoring a patient's electrocardiogram (ECG) data using a hand-held computer in association with a wireline or wireless telephone system.

2. Description of the Prior Art

The prior art includes numerous systems wherein ECG data or the like is transmitted from a patient to a particular doctor's office or health service center. U.S. Pat. No. 4,938,229 discloses an earlier form of monitoring system which includes apparatus for demodulating a constant amplitude audio FM ECG signal. The analog FM signal is processed through a zero crossing counter which generates a digital pulse for every crossing. The time intervals between pulses are then averaged to produce a digital ECG signal at a predetermined sample rate. This procedure differs from the present invention as it does not digitize the audio FM signal, nor does it utilize such as a polyphase demodulator to derive the ECG data in digital form. U.S. Pat. No. 4,531,527 discloses another system for transtelephonic ECG monitoring; however, this system requires special hardware considerations and differs in may other aspects from Applicants' method and apparatus.

U.S. Pat. No. 4,409,984 discloses a method for square pulse frequency modulation and demodulation of ECG data in a multiple patient monitoring system. The system does not employ polyphase demodulation since it processes a constant amplitude FM signal to detect zero crossings, and neither does it provide portable storage and display of ECG data in the manner of the present invention. The similar digital FM demodulator is taught in the U.S. Pat. Nos. 4,027,146 and 3,909,599, but there is no teaching of the digitization of an FM data signal nor of possible retransmitting of the FM signal. In addition, these patents all require hardware of specialized design for carrying out specific circuit functions.

The U.S. Pat. Nos. 5,365,935; 5,191,891; and 5,333,616 all relate to an ECG monitoring system that utilizes wrist-worn transtelephonic ECG recorders and transmitters. The disclosure does not deal with any form of signal demodulation and display or any storage and retransmission capabilities. The present invention would be compatible for use to receive, display, store and/or retransmit biomedical signals derived by the teachings of these patents.

ECG data is usually transmitted directly from the patient to the analyzing location and one such system, available from Instromedix, Inc. of Hillsboro, Oreg., utilizes a Heart Card to provide a recording of the ECG signal from thirty seconds upward to five minutes. This system provides for transmission via a wired or wireless telephone system of such recorded or realtime ECG data in the form of a frequency modulated audio signal. The transmitted FM audio signal is then demodulated at the doctor's office or health service center for viewing of the actual ECG data whereupon the patient's personal doctor is alerted if a problem is seen in the data. Further, the actual ECG data waveform may be sent via facsimile to the attending doctor.

SUMMARY OF THE INVENTION

The present invention relates to an improved communication system for conveying ECG data or other biomedical waveform data more directly between the patient and an attending doctor's location. The patient employs a Heart Card-type of device that converts the patient's ECG signal into a frequency modulated audio signal that may then be analyzed by audio inputting via a telephone system to a selected hand-held computer device that functions to digitize, record and demodulate the frequency modulated signal for presentation and viewing on the hand-held computer display screen. Also, the operator has the option of printing out the demodulated biomedical signal for further viewing separate from the hand-held computer. There is still further an option of retransmitting the stored ECG audio signal via telephone, either wireline or wireless, to a designated doctor's office; or, if no one answers, the call may be forwarded to another nurse or doctor as designated. At any of the first or forwarded receiver stations, the attendant may also have a programmed hand-held computer that can receive the audio FM biomedical signal for digitization, recording and demodulation for viewing. The hand-held computer is one with integrated microphone, audio analog to digital converter, digital to analog converter, speaker, and central processing unit with memory for performing various computational, data storage and signal processing tasks.

Therefore, it is an object of the present invention to provide a highly accurate and portable biomedical signal monitor for use with a telephone system, either wireline or wireless.

It is also an object of the present invention to provide a highly accurate and reliable patient monitoring system that allows the doctor to interface directly over a telephone system with the patient at anytime or anywhere.

It is yet further an object of the present invention to provide a patient monitor system that may be quickly and reliably deployed in monitoring operation.

It is still further an object of the present invention to provide a reliable and accurate patient ECG monitoring system with first hand communication between doctor (or other healthcare provider) and patient.

Finally, it is an object of the invention to provide a hand-held computer with proprietary software that combines with a telephone system to provide remote monitoring of a patient's electrocardiogram (ECG).

Other objects and advantages of the invention will be evident from the following detailed description when read in conjunction with the accompanying drawings that illustrate the invention.

BRIEF DESCRIPTION OF THE DRAWINGS

FIG. 6 is a diagram illustrating cycle accumulation between filtered data and decimated data output;

FIGS. 7, 8 and 9 are a flow diagram for the demodulation procedure carried out by the Rhythm-Stat SX software.

DETAILED DESCRIPTION OF THE INVENTION

Figure 1:
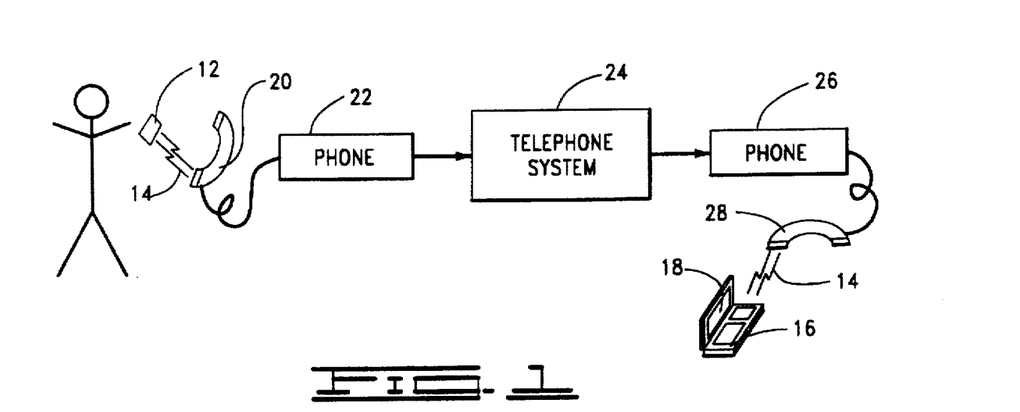
FIG. 1 is an idealized block diagram of an ECG monitoring system.

Referring to FIG. 1, a patient monitoring system 10 consists of a Heart Card 12 disposed on the patient and capable of detecting and recording the electrocardiogram signal (ECG) for a predetermined time and then actuable to transmit the ECG as a frequency modulated audio band signal 14. The Heart Card 12 is a commercially available device that functions to sense the ECG data for a predetermined time period and, after the period, the Heart Card 12 can be actuated to transmit the audio frequency modulated ECG data. Such Heart Card sensor/transmitters may be obtained from such as Instromedix, Inc. of Hillsboro, Oreg. Other devices that perform the same or similar functions (i.e., recording the ECG and transmitting over a phone system as a frequency modulated audio signal) are available from Instromedix, Inc. and other vendors.

The frequency modulated audio signal 14 may then be transmitted via telephone, either wireline or wireless; or, the frequency modulated audio signal 14 may be played directly into the audio microphone of a palmtop computer 16 which includes resident software that processes the biomedical data contained in the frequency modulated audio signal and displays the data on the computer screen 18. In most cases, the patient and Heart Card 12 will be remote from the palmtop computer 16 and the attending physician or diagnostician. In this situation the Heart Card 12 need only transmit the frequency modulated audio into the receiver 20 of telephone 22 which is connected via a suitable telephone system 24, either wireline or wireless, to a telephone 26 at the attending physician's office whereupon the telephone transmitter 28 can direct frequency modulated audio data 14 into the microphone of the palmtop computer 16 to complete the information relay.

A preferred embodiment of the invention uses a Psion 3a palmtop personal computer with proprietary software as will be further described. The hand-held computer 16 must have an integrated microphone or direct audio electrical jack that can interface to a wireline or wireless phone. A laptop computer could be used for the present invention; however, it does not have the portability feature that makes the hand-held version preferred.

Figure 2:
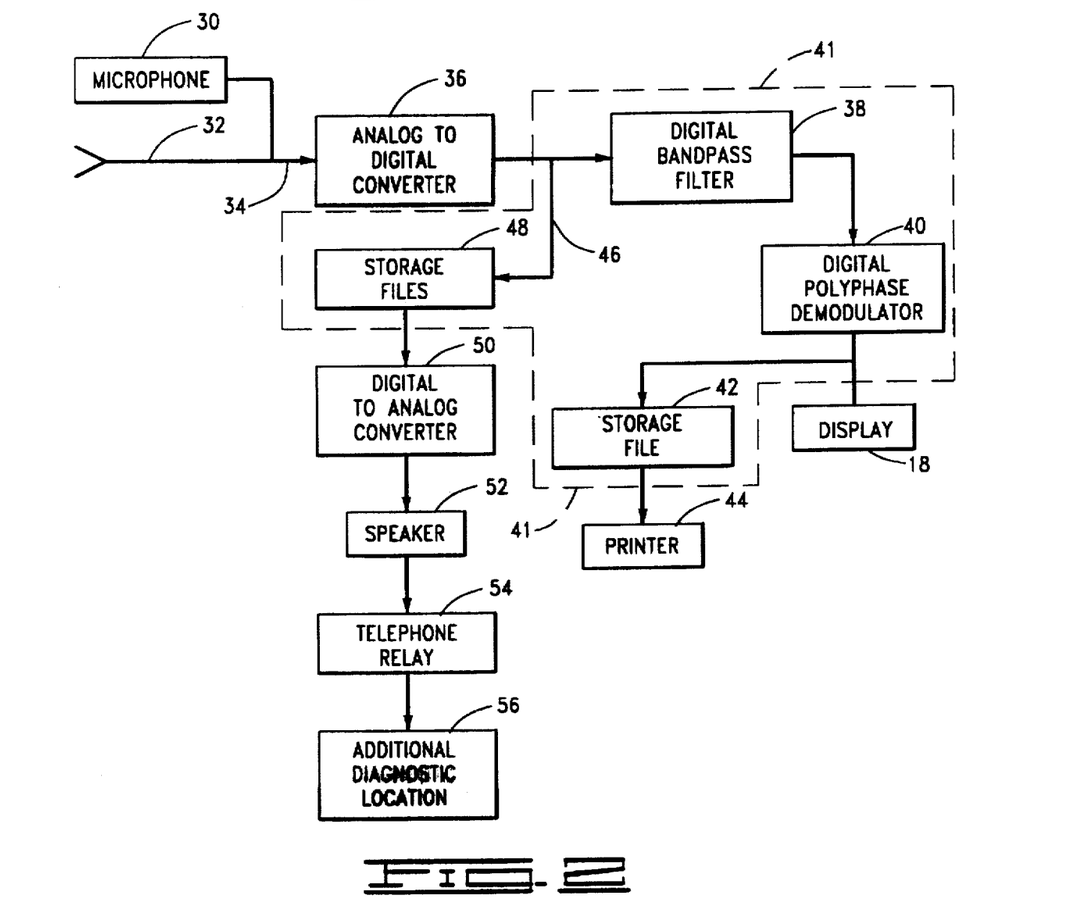
FIG. 2 is a functional block diagram of a preferred form of signal processing circuitry as effected by a hand-held computer.

The preferred form of the invention is illustrated in the functional block diagram of FIG. 2 which illustrates the functional components of the programmed Psion 3a palmtop computer 16. The frequency modulated audio biomedical data may be input directly to microphone 30 or, in some cases, it may be received directly through a connector jack 32 to input lead 34 to analog/digital converter 36. The output from analog to digital converter 36 is then applied to a digital band-pass filter 38, e.g., over the band of 0.05 Hz to 40 Hz, and then to a digital polyphase demodulator 40. The dash-line 41 outlines the central processing unit and memory components of the palmtop computer 16 (FIG. 1). The demodulator 40 employs two simultaneous filters which have been optimized for integer operation using a micropower microprocessor. The output from demodulator 40 may then be applied directly to display 18, or the filtered digital signal can be applied directly to a storage file 42 for selected output via printer 44.

Figure 3:
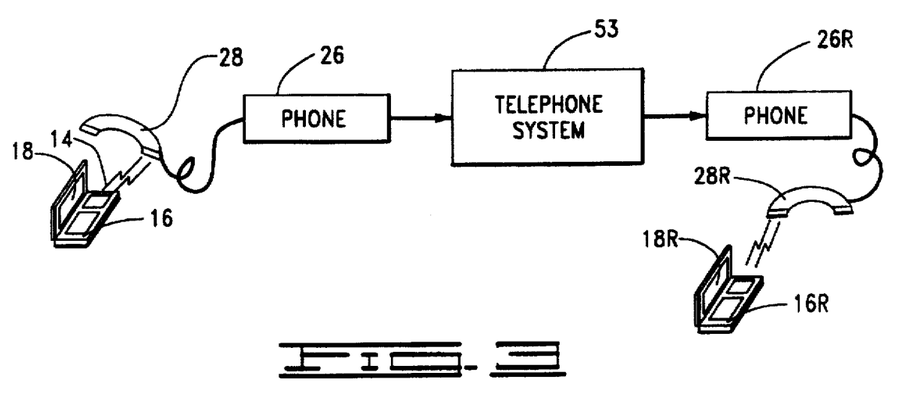
FIG. 3 is an idealized block diagram of a monitoring relay link for further transmission of ECG data.

Alternatively, the digital biomedical FM data signal output from analog to digital converter 36 may be applied via lead 46 to a storage file 48. Selected data from storage file 48 may then be played back into digital to analog converter 50 and the analog signal can then be applied to a loud speaker 52 and/or further telephone or facsimile relay 54 to a remote diagnostic location for further demodulation, review and opinion. As shown in FIG. 3, the original receiving phone 26 and handset 28 may be used to relay the data via telephone system link 53 to yet another phone 26R and handset 28R as located at another remote location. Such further transfer may be necessitated by a need for second opinion or additional comparison data. The hand-held computer 16 may be operated to emit the audible ECG data from handset 18 for transmission via telephone interconnect 53 to the remote phone 26R whereupon handset 28R provides audible input to another hand-held computer 16R for processing and display of the ECG data.

Figure 4:
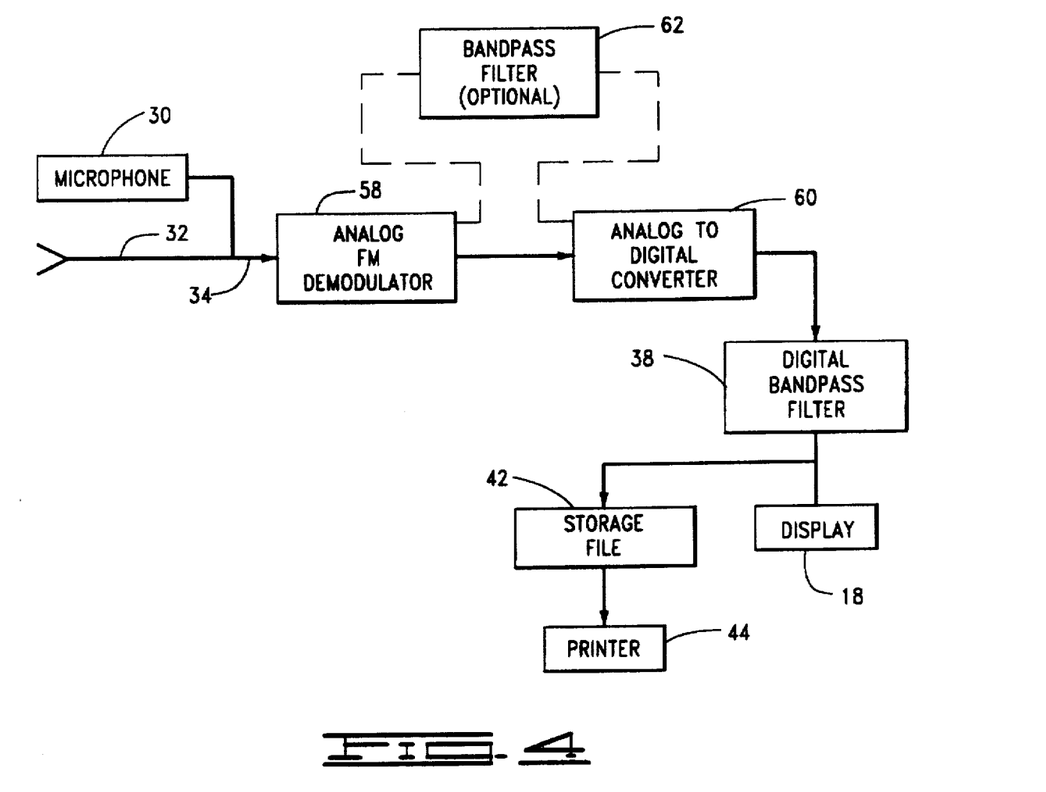
FIG. 4 is a functional block diagram of an alternative form of patient monitoring circuitry as effected by a programmed hand-held computer.

FIG. 4 illustrates an alternative design of the invention utilizing a palmtop computer of the type having a PCMCIA interface slot for signal processing and display. A received frequency modulated audio signal is fed either via microphone 30 or connector 32 to input lead 34 to the analog FM demodulator 58. The FM demodulator 58 may be such as a IC phase locked loop, Exar type 215. The analog FM demodulator 58 then applies output to an analog to digital converter 60 which provides digital output via the palmtop PCMCIA interface to the palmtop's CPU for digital filtering (40), storage and display. Optionally, a band-pass filter 62 may be interconnected between the demodulator 58 and the analog to digital converter 60. The output from digital filter 38, having a pass-band of 0.05 Hz to 40 Hz., may then be applied to output display 18, or, it may be placed in storage file 42 for subsequent recall to printer 44. The demodulator 58, converter 60 and bandpass filters 62 and 40 are all contained in the PCMCIA card.

Figure 5:
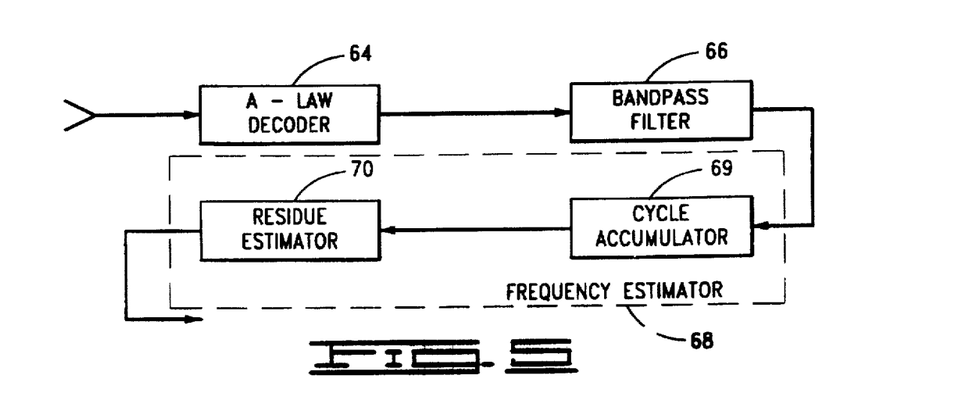
FIG. 5 is a diagram of a programmed signal process as utilized in the preferred form of circuitry.

Referring to the preferred embodiment of FIG. 2, it is an objective of the Rhythm-Stat program to demodulate a frequency modulated audio signal and to decimate the output for storage and plotting purposes. The Psion 3a computer 16 records sound files at an 8,000 samples per second rate and uses an A-Law analog to digital transformation. Therefore, the program used to demodulate a frequency modulated ECG or biomedical signal must perform three functions. As shown in FIG. 5, these functions are (1) an A-Law decoder 64, (2) a band-pass filter 66, and (3) a frequency estimator 68 which includes a residue estimator 70 and a cycle accumulator 69. The A-Law decoder 64 functions as an expander which reverses the action of the A-Law compressor in the Psion. The A-Law encoding is a standard approximation to the logarithmic compression as established by CCITT, the European standards body. The output of the A-Law compander is defined by $$F(x) = sgn(x) * A|x|/(1 + ln(A))$$

$$0 \leq |x| < 1/A \quad (1)$$

$$F(x) = sgn(x) * (1 + ln(A|x|))/(1 + ln(A))$$

$$1/A \leq |x| \leq 1 \quad (2)$$

where x is the analog input, F(x) is the A-Law compander output, sgn(x) is the sign (±) of x, and A is the compression parameter. Since the Psion 3a computer 16 records the sound file in A-Law encoded format (12-bit data stored in 8 bits, all at 8000 samples per second), these values need to be decoded in order to band-pass filter and demodulate the signal. The decoding is accomplished by using a look-up table. The range of A-Law encoded values is −128 to 127, therefore, an array of length 256 is initialized to contain the A-Law decoded values. The array is indexed from zero to 255 as the decoded value contained at indexed zero corresponds to the A-Law value of −128, and the decoded value contained at index 255 corresponds to the A-Law value of 127. Therefore, to decode any A-Law value, 128 is added to the A-Law value and the result is used to index into the array.

The digital band-pass filter 66 is utilized to remove unwanted signal introduced when recording with the Psion 3a. The equation used to realize the band-pass filter is $$a_0 y(n) = b_0 x(n) + b_1 x(n-1) + b_2 x(n-2) + a_1 y(n-1) + a_2 y(n-2) \quad (3)$$

where $x(n)$ is the input data, $y(n)$ is the output data, and $a_x$, $b_x$ are constant coefficients. For data that is sampled at 8000 Hz, to obtain a band-pass filter with a Q=2 and a center frequency of 2000 Hz, the coefficients are set to $a_0 = 1$
$a_1 = 0$
$a_2 = -0.5$
$b_0 = 1$
$b_1 = 0$
$b_2 = -1$ This realizes a band-pass filter with a transfer function $$H(z) = (1 - z^{-2})/(1 + 0.5 z^{-2}) \quad (4)$$

This portion of the demodulation procedure is implemented directly after the A-Law decoder 64 and before the cycle counting procedure.

The frequency estimator 68 functions by windowing the input data and counting the number of complete cycles contained within the window. The phase of the incomplete cycle located at the end of each window is estimated by using the arctangent function. Therefore, the frequency estimator 68 contains two sections which are (1) the cycle accumulator and (2) a residue estimator. See FIG. 6. The cycle accumulator consists of two overlapping windows and FIG. 6 shows the relationship between the two windows. The filtered data appears on line 72 with 40 unit graduations while the decimated output data appears along line 74. The size of each window determines the amount of decimation in the demodulation procedure. Choosing a window size of 80 decimates the data from 80 input points to 1 (80:1), however, with two overlapping windows the final output is decimated by 40:1. Thus, with an original sampling of 8000 samples per second, the output is resampled to 200 samples per second after decimation. For a frequency estimate, each window counts the number of complete cycles of 80 bandpass filtered data points. For each complete cycle, 256 (corresponding to $2\pi$ radians) is added to the window counters. After determining the number of complete cycles contained in 80 data points, a window calls the residue estimator passing the 79th and 80th data points to determine the amount of the incomplete cycle on the end of the window.

Using the last two data points of the cycle accumulator window, the residue estimator 70 determines the amount of an incomplete cycle by using a look-up table technique. The look-up table contains arctangent values for every possible point in the first quadrant of a sine wave. The values are scaled to range from zero to 64 (corresponding to $0 - \pi/2$ radians). Using the sign of the two points passed from the cycle counter, the residue estimator 70 determines in which quadrant the points are located. These points are then scaled so that both are less than 64 in order to index into the arctangent look-up table. The quadrant determination with the arctangent value, determines the output of the residue estimator as follows:

1st quadrant: Residue Estimate=arctangent value
2nd quadrant: Residue Estimate=128 −arctangent value
3rd quadrant: Residue Estimate=128 +arctangent value
4th quadrant: Residue Estimate=256 −arctangent value The residue estimate is added to the window calling the residue estimator 70 and thus is used as an output point. The window counter is then reset to 256 minus residue estimate to include an estimate of the incomplete cycle located at the beginning of the next 80 filtered data points.

Figure 7:
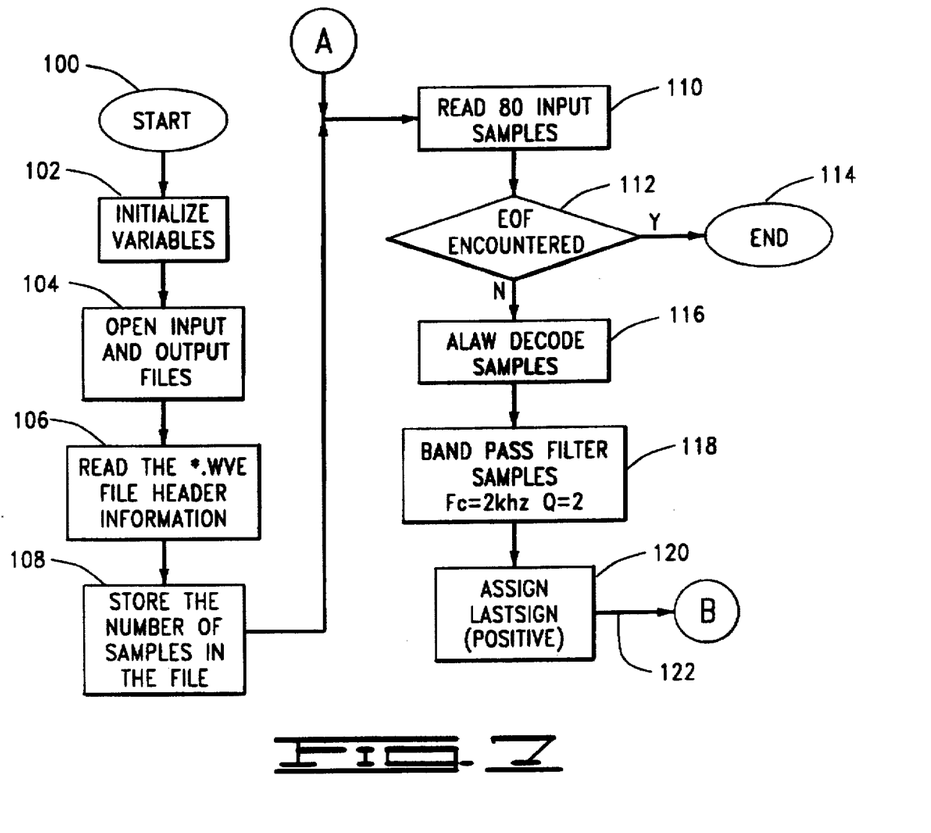
Figure 9:
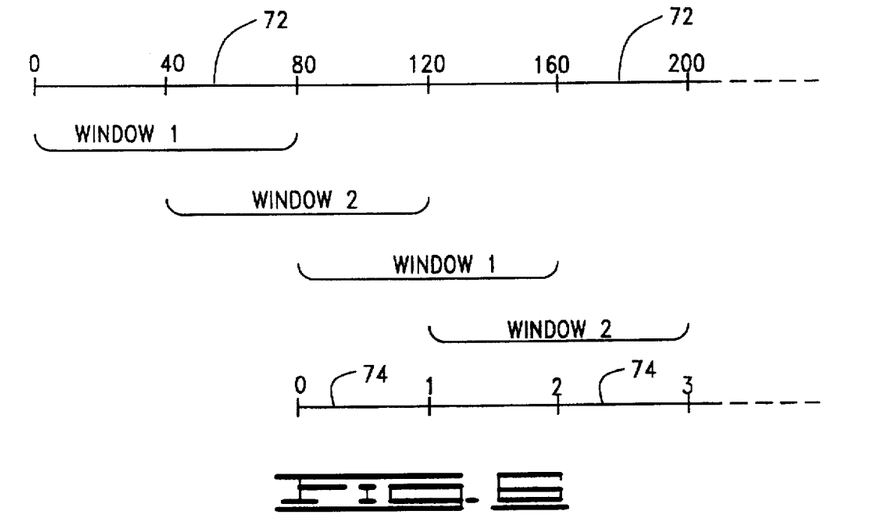

FIGS. 7, 8 and 9 are a flow diagram of the demodulation procedure that is carried out under the system program, i.e., the Rhythm-Stat XL software, as will be further described below. In FIG. 7, the process begins at START 100 whereupon variables are initialized in flow stage 102 and the input and output files are readied at stage 104. The flow stage 106 then reads the *.WVE file header information and the number of samples in the file is stored at flow stage 108. Flow stage 108 then proceeds to stage 110 which sees reading of eighty input samples after which decision stage 112 tests to see whether or not end of file (EOF) has been encountered. If end of file does appear, then the affirmative output proceeds to END stage 114 and completion of the program operation. If end of file is not yet reached, the negative output passes flow to stage 116 which functions to A-Law decode the samples. The A-Law decoding expands the A-Law encoded values to the original value.

Data handling proceeds to flow stage 118 which effects bandpass filtering and subsequent flow stage 120 functions to assign samples in accordance with polarity of the last sign. Continuing on to FIG. 8, the line 122 connects from Terminal B to flow stage 124 which points to first sample with data flow on line 126 to a series of decision stages. A first decision stage 128 tests for whether or not the sample is positive with a negative response by-passing on line 130, and an affirmative response proceeding to the subsequent decision stage 132 which queries for last sign negative. A negative response directs flow to by-pass line 130 and an affirmative response continues process to stage 134 which adds 256 to cyclecount 1 and cyclecount 2. A flow stage 136 then assigns a lastsign the sign (±) of the sample being processed.

Flow line 138 then proceeds to stage 140 which functions to point to the next sample prior to decision stage 142 which queries whether the sample is the forty-first sample in the sequence. If negative, and the sample is other than the forty-first sample, flow recycles via line 143 to the decision stage 128 which tests whether or not the sample is positive; but, if stage 142 is affirmative, flow proceeds to stage 144 wherein the look-up cycle residue is estimated. That is, a value is obtained from the arctangent table for samples thirty-nine and forty as flow proceeds to stage 146 which adds the estimate to cyclecount 1. A next flow stage 148 sees output to file of cyclecount 1 with flow stage 150 resetting the cyclecount 1 before proceeding on line 152 for connection to the C terminal at FIG. 9.

The line 152 leads to a series of decision stages wherein stage 154 tests for a positive sample and, if negative, cycles ahead via line 156, and, if affirmative, query is made of the next decision stage 158 as to whether or not the last sign was negative. If not, cycle ahead via lead 156 is made or, if affirmative, flow proceeds to stage 160 which adds 256 to each of cyclecount 1 and cyclecount 2.

Flow proceeds from stage 160 as well as by-pass line 156 to a stage 162 which functions to assign the lastsign or previous sample sign. Thereafter, flow stage 164 points to the next sample as indication proceeds via line 166 to a decision stage 168 which queries whether the sample is the eighty-first sample in the succession. If not, flow proceeds via line 170 to recycle through stages 154 and 158 and succeeding stages; however, if the decision is affirmative (the eighty-first sample) then stage 172 establishes the look-up cycle residue estimate, i.e., samples 79 and 80 from the arctangent look-up table. The estimate is added to the cyclecount 2 in flow stage 174 and output to file in flow stage 176 prior to the reset of cyclecount 2 in stage 178. Flow then proceeds through terminal A back to FIG. 7 for recycle through flow stage 110 which reads the next eighty input samples. Eventually, when end of file is encountered as at flow stage 112, the affirmative output proceeds to END 114 to terminate the process.

The program for controlling the Psion 3a hand-held computer 16 is termed the Rhythm-Stat XL software and it functions to acquire frequency modulated biomedical data, e.g., ECG data, as generated by an Instromedix™ recording device known as the Heart Card 12 or other similar medical data recording device. The Psion 3a computer 16 is programmed with the Rhythm-Stat XL program that functions with the Psion floating point emulator. Data files with a *.WVE extension must be first placed in the ECG data directory, and these are Psion sound files that will be decoded, demodulated, and displayed by the Rhythm-Stat XL program as an ECG rhythm strip.

Figure 10:
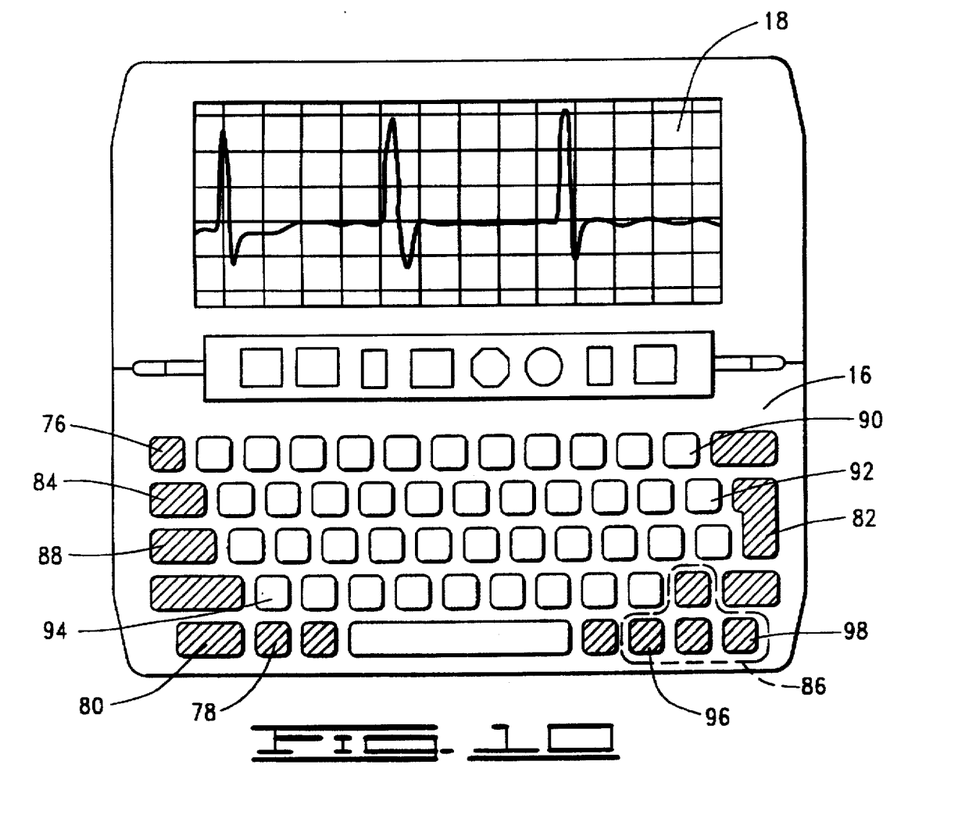
FIG. 10 is a top plan view of a Psion 3a hand-held computer.

On start up (see FIG. 10), the program displays a title screen, and pressing the ESCAPE key 76 continues operation with an empty graphics grid as the program title will appear on display screen 18. The MENU key 78 may then be depressed to access the program menus and selected hot keys will be shown to the right of the listed menu items. In order to use an item, it is necessary to hold down the Psion special key 80 while pressing the desired character key. As shown in FIG. 10, the white keys are the standard Qwerty keys while the black keys are various function and control keys. The ECG data scaling, keyboard display controls, and data acquisition and relay are summarized below.

The initial display represents a 12.5 mm/second scale that is divided into 200 ms graduations. Up to three 9.6 second periods of ECG totalling 28.8 seconds of ECG rhythm, may be displayed. Expanded scales of 25 and 50 mm per second are available.

The y scale is calibrated to show millivolts of signal value. During demodulation, and after the processing is completed, and the data replotted, a square calibration pulse will appear on the left of the first segment of ECG data to provide signal calibration. An additional calibration pulse may be found at the end of a data set and these calibration pulses are nominally 1 millivolt on the y axis. A control key selects display scales of 25 or 50 mm per second and selected arrow keys 86 may be used to select ECG epochs for display. When the ECG is expanded on the x axis, the y scale is 0.5 millivolts per graduation, and left and right arrow keys 96 and 98 will scroll the expanded display by one epoch at the selected scale. The user may increase or decrease the waveform amplitude by a factor of two with selected gain controls at any scale. The waveform may be shifted up or down in 0.5 mv increments with up and down arrow keys of key group 86 for expanded displays, and also with the shifted up and down arrow keys in the initial 12.5 mm per second display.

The Rhythm-Stat XL program records, decodes and displays acoustic frequency modulated ECG data that is generated by such as the Instromedix Heart Card or other heart watch device, or by another Psion 3a computer that is equipped with Rhythm-Stat XL program, as shown in FIG. 3. Recording of the acoustic data may be direct, or it may be done with ordinary telephones across a wire line or wireless phone system.

A more detailed operation description of menu options, keyboard controls, and ECG recording and relay procedures for this program follows. A first option in the FILES menu is the "open ECG file" which functions to display a list of files in the reverse/ECG directory. Left and right arrow keys 96 and 98 at the files display will present the file names. The only valid file types are *.RXL, *.RST and *.WVE files, and if other files are in the ECG directory, they will be shown. The program has no provision for user interruption of .WVE input file processing, which takes about 30 seconds, or of ECG data recording or playback, which takes 35 seconds. If necessary, a user may terminate the application during file processing or recording by holding down the Psion control key 80 while depressing the ESCAPE key 76.

The Rhythm-Stat XL program is intended to record and display frequency modulated acoustic ECG data, and taking the record option will produce a file name selection dialogue. When the desired file name is entered, a screen will tell the user that Rhythm-Stat XL program is ready to record and will begin when the "ENTER" key 82 is depressed.

At this point, the user can place the output speaker on the Heart Card 12 as close to the Psion microphone opening (square opening at bottom right edge of the case) as possible. If recording over the telephone, place the Heart Card 12 (FIG. 1) on the sender's handset microphone 20 with the receiver's handset speaker 28 as close to the Psion microphone opening as possible. The user can then initiate the playback and recording as close to simultaneously as possible. The Heart Card 12 has a nominal 30 second playback period while the Psion 3a records 35 seconds of sound. The difference will accommodate a few seconds of variance in user synchronization of playback and recording.

Note that there is no progress indicated for the recording and the program, and when Rhythm-Stat XL program completes its recording, an annunciator chirps, and a third screen appears to tell the user that the recording is complete. The new WVE file will then be found among the file names offered in the files plus open menu option for processing and display.

Another files menu item, playback ECG, appears in the Rhythm-Stat XL program. Thus, the program may be used to relay the FM ECG data to another Psion equipped with the Rhythm-Stat XL program, by playing back the *.WVE ECG data file. Taking the playback option will produce a file name selection dialogue. Once the file name is selected, a second screen will tell the user that Rhythm-Stat XL is ready to play back the ECG data file, and will begin when the ENTER key 82 is depressed. The receiving Psion must be prepared for recording with the output speaker on the sending Psion as close to the microphone opening of the receiving Psion as is conveniently possible. If relaying the data over a phone system, the sending Psion speaker should be placed closely over the handset microphone with the receiving handset speaker as close to the related Psion opening as possible. Once again, the playback and recording is initiated as close to simultaneously as possible and a high frequency warble of the frequency modulated ECG data will be audible and ceasing upon completion of playback. An annunciator chirp tells the user when the transfer has been accomplished.

The remaining files menu items are "SAVE ECG AS", "DELETE", and "EXIT" and the last two items are self-explanatory. However, the "SAVE AS" item provides for automatic conversion of WVE files to RST files. The data output remains the same, but the RST files are 1 k to 5 k as compared to 250 k for the WVE files. It is useful to be able to process the same WVE file in different ways in order to examine development options.

In addition to the files menu, there is a waveform menu which controls certain display parameters. A first "EXPAND ON X" refers to selection of 25 or 50 mm/second displays. Note that pressing the "z" key 94 will have the same effect. When "EXPAND ON X" item is first activated, a 4.8 second epoch will be highlighted on the main 12×5 mm/second display screen. Pressing "z" key 94 again will then toggle the selection box back and forth between the 4.8 second epoch (25 mm/second) and a 2.4 second epoch (50 mm/second). The selection block may be moved around with selected arrow keys 86. Pressing "ENTER" key 82 will display the epoch at the selected mm/second x-axis scale, and pressing the "z" key 94 will toggle the expanded or zoom selection, from 25 mm/second to 50 mm/second and back. The time period in the waveform and the scale are displayed in a text window at the top of the display screen 18. While in a 25 or 50 mm/second screen, the left and right arrow keys 96 and 98 will scroll the display to the left or right; and, a shifted left or right arrow will increment or decrement the display one complete epoch to the left or right. Depression of control key 88 plus a left or right arrow of keys 86 will initiate continuous scrolling that may be terminated with the "ESCAPE" key 76.

If not scrolling continuously, the "ESCAPE" key 76 will return the user to the 2.5 mm/second main display screen for alternative epoch selection. While zoomed, the dual function Home keys 96 and end key 98 (the Psion plus left arrow and Psion plus right arrow of keys 86) will display the first and last epoch at the scale selected. The up and down arrow keys of the group 86 will shift the zero volt baseline up or down.

Since the nominal recording and playback periods for Rhythm-Stat XL are 35 seconds, additional ECG data, beyond the 28.8 seconds shown on the initial 12.5 mm/second screen, may be available. In such case, that data may be accessed easily by selecting the last epoch on the 12.5 mm/second screen, pressing enter, and scrolling to the right to the end of the data set. Should the user make a recording synchronization error, an additional 1 millivolt calibration pulse may be found at the end of the data set.

Waveform gain selection is accomplished using the Psion key 80 plus the + key 90 to increase the current waveform amplitude by a factor of 2. The waveform amplitude can be halved by depressing the Psion key 80 plus the – key 92. It should be noted that reducing the gain, and then increasing the gain, may cause loss of detail resolution. Similarly, increasing the gain may produce values that are detrimental to ECG feature resolution; however, the file may be processed again to regain an original waveform for further manipulation.

There is a waveform menu for moving the ECG up and down on the display screen 18. In a zoomed screen, the menu selection, or an up or down arrow of keys 86 will move the waveform up or down on the display adjusting the position of the zero millivolt baseline. This function is useful on occasions where a low frequency component places a portion of the ECG off the screen in the 25 or 50 mm/second display. In the 12.5 mm/second screen, the same effect may be obtained by the menu selection of the Psion control key 80 plus a shifted up or down arrow key of the key group 86.

The complete program of source code files for Rhythm-Stat XL version 0.2.8 alpha is included with the present application as Exhibit A. A list of the major software routines with functional description is as follows:

```
! read me
Source Code files for Rhythm-Stat XL
ABOUT.C
  Title and About screen
Common.C
  These are variables and structures for global reference
DeMod.Asm
  Assembly module for demodulation of acoustic FM ECG signal,
  Requires pointers to ALAW decoding and Arctangent tables; Called by
  Process_WVE_File ( ) in WVE_File.C.
Dlg_Ctl.C
  file dialog control
File_Ctl.C
  UBYTE Open Sound File (UBYTE File Name [ ]);
  VOID Close Sound File (VOID);
  UBYTE Read Sound Header (SndFile sFileHead);
  INT Read Sound Segment (UBYTE FileBuf [ ], UINT Size);
G_SCROLL.C
  Scrolls graphics plotting rectangle, one 200 ms window at a time,
  right or left
GRID_CTL.C
  Entire screen is MainRcl.
  Application screen AppRel is the MainRcl, less border
  Plotting area is PltRcl, which is AppRcl less axes and caption, x
  and y values are in absolute screen coordinates
MISC.C
  Miscellaneous functions and procedures
NOTIFY.C
  Procedures for posting model and non-model message boxes for user.
PLOT_CTL.C
  Procedures for plotting epochs, and entire data set on the 12.6
  mm.sec screen.
PPP_Dec.C
  Procedures to decimate (downsample) data, while locating and
  preserving peak information in the waveform. External call is made
  to PPP_Decimate_into_Buffers ( ) from WVE_File.C
PPP_Dec.H
  Include file for module PPP_Dec.C
Notify.C
  Procedures for posting model and non-model message boxes for user
PLOT_CTL.C
  Procedures for plotting epochs, and the entire data set on 12.5
  mm/sec screen
PPP_Dec.C
  Procedures to decimate (downsample) data, while locating and
  preserving peak information in waveform. External call is made to
  PPP_Decimate_into_Buffers ( ) from WVE_File.C
PPP_Dec.H
  Include file for module PPP_Dec.C
PVTYPES.H
  Include file for module RST_File.C
RST_File.C
  Procedures to read and process a *.RST file format. The *.RST file
  format is a variation on the *.CMF file format used in other Data
  Critical medical information files.
RSTAT_XL.H
  Include file for Rhythm-Stat XL modules
WVE_File.C
  Procedure to decode and demodulate the FM ECG signal, received as
  sound data
Wnd_Ctrl.C
  The entire screen is MainRcl. The Application Screen, AppRcl, is
  the MainRcl, less the border. The plotting area is PltRcl, which
  is AppRcl, less axes and Caption. X and Y values are in absolute
  screen coordinates
Str_Fn.C
  String manipulation functions and utilities
Sound_IO.C
  Procedures to record and playback the FM modulated ECG data in the
  form of Psion WVE sound files
```

The foregoing discloses a novel method and apparatus using a programmed palmtop computer that enables a patient to monitor his own biomedical data for dial-up phone relay to his primary doctor or other diagnostician. The patient can detect and record up to 5 minutes of a selected ECG rhythm sequence for transmission via frequency modulated audio signal to the programmed computer which then functions to digitize and demodulate the rhythm sequence for print-out on the palmtop computer display or printing device.

The present invention removes intervention of a third party in the monitoring service and allows a medical attendant familiar with the patient to interface directly with that patient. In other words, an attending doctor or medical provider can offer more personal and more rapid attention to each case.

The present device enables a virtual arrythmia monitoring service whereby an attending physician can receive and review transtelephonic ECG data using only a hand-held computer and a phone, either wireline or wireless.

Changes may be made in the combination and arrangement of elements as heretofore set forth in the specification and shown in the drawings; it being understood that changes may be made in the embodiments disclosed without departing from the spirit and scope of the invention as defined in the following claims.

What is claimed is:

1. A hand-held computer device for patient monitoring, comprising:
   a palmtop digital computer that includes microphone means for receiving a frequency modulated audio signal indicating a selected, continuously variable biomedical parameter of a patient's physical condition;
   analog to digital converter means changing the frequency modulated audio signal to a digital signal;
   means for band-pass filtering said digital signal to produce a filtered digital signal having a low frequency pass-band;
   a digital polyphase demodulator receiving said digital signal for transformation to a de-modulated digital signal; and
   means for displaying the filtered digital signal for a selected time interval.

2. A hand-held computer device as set forth in claim 1 which further includes:
   storage means receiving said filtered digital signal to file in storage.

3. A hand-held computer device as set forth in claim 2 which further includes:
   means for conducting a selected digital signal from said storage for direct print-out.

4. A hand-held computer device as set forth in claim 2 which further includes:
   means for conducting a selected digital signal from said storage via a telephone facsimile system.

5. A hand-held computer device as set forth in claim 1 which further includes:
   file means receiving said digital signals from said analog to digital converter means for storage of selected digital signals;
   digital-to-analog converter means receiving stored digital signals from the file means to produce a selected time analog signal; and
   speaker means for annunciating said time analog signal for pickup and relay via a telephone connection to an auxiliary hand-held computer device.

6. A hand-held computer device as set forth in claim 1 wherein said means for receiving comprises:
   a receptacle receiving electrical signal input of said frequency modulated audio signal.

7. A personal cardiac monitoring system, comprising:
   a palmtop computer having a microphone providing input to an analog to digital converter;
   said palmtop computer also having a digital to analog converter, a speaker and a display screen connected for visual and audible signal output, respectively, from a central processing unit with associated memory containing resident software, and further comprising:
   means detecting and audibly reproducing a patient's ECG segment for a predetermined time interval as frequency modulated audio for input to said computer microphone; and
   a digital polyphase demodulator controlling the demodulation of digital signals from the analog to digital converter for output to said display screen.

8. A personal cardiac monitoring system as set forth in claim 7 which further includes:
   a low frequency band-pass filter receiving said converted digital signal output from the analog to digital signal convertor and outputting to said digital polyphase demodulator.

9. A personal cardiac monitoring system as set forth in claim 7 which further includes:
   means receiving said low frequency band-pass filter output for audible output from said hand-held computer speaker; and
   an associated telephone for pick-up of said audible output to provide a relay extension.

10. A hand-held computer device for patient monitoring, comprising:
    means for receiving a frequency modulated audio signal indicating a selected biomedical parameter of a patient's physical condition;
    means for digitizing and A-Law compressing said audio signal to provide an A-Law digital output;
    A-Law decoder means receiving and expanding said A-Law digital output;
    a band-pass filter receiving said expanded digital output to produce a filtered digital output;
    a frequency estimator means receiving said filtered digital output; and
    means for displaying said filtered digital output.

11. A hand-held computer device as set forth in claim 10 wherein said frequency estimator means comprises:
    a cycle accumulator receiving said filtered digital output and producing an accumulator signal; and
    a residue estimator receiving said accumulator signal to produce said filtered digital output.

12. A hand-held computer device as set forth in claim 11 wherein:
    said selected biomedical parameter is a patient's ECG rhythm strip.

13. A method for monitoring a patient's ECG signal, comprising:
    developing a frequency modulated audio ECG signal from the patient;
    inputting the frequency modulated audio ECG signal via telephone to a programmed palmtop digital computer at a medical diagnostics site;
    converting said frequency modulated audio ECG signal to a digital frequency modulated ECG signal;
    demodulating said digital frequency modulated ECG signal to produce a digital ECG signal; and
    displaying said digital ECG signal as a time analog indication.

14. A method for using a hand-held palmtop computer for monitoring a patient's ECG signals, comprising:
    developing a frequency modulated audio ECG signal from the patient;

inputting the frequency modulated audio ECG signal via telephone to a palmtop, programmed digital computer at a medical diagnostics site;

companding said frequency modulated audio ECG signal by transforming with an A-Law encoder and decoder to produce an A-Law digital signal counterpart;

filtering said digital signal counterpart with a selected bandpass; and deriving a frequency estimate of the digital signal counterpart for display of the ECG signals.

* * * * *